United States Patent [19]

Zichis

[11] 4,092,409

[45] May 30, 1978

[54] METHOD FOR THE DIAGNOSIS OF VIRAL DISEASES

[75] Inventor: Joseph Zichis, Chicago, Ill.

[73] Assignee: Beckman Instruments, Inc., Fullerton, Calif.

[21] Appl. No.: 397,253

[22] Filed: Sep. 14, 1973

Related U.S. Application Data

[60] Division of Ser. No. 112,039, Feb. 2, 1971, Pat. No. 3,777,014, which is a continuation-in-part of Ser. No. 786,770, Dec. 24, 1968, abandoned.

[51] Int. Cl.$^2$ ................ G01N 31/00; G01N 33/16
[52] U.S. Cl. .......................... 424/12; 424/8; 424/13; 424/89
[58] Field of Search ................ 424/3, 8, 12, 89

[56] References Cited

PUBLICATIONS

Milgrom, Virology, vol. 33, 1967, pp. 145–149.
Isliker, Annals of The N.Y. Acd. Sci., vol. 57, Art. 3, Nov. 11, 1953, pp. 225–238.
Lennette, Diag. Proc. for Viral & Rickettsal Dis., Amer. Pub. Health Asso., N.Y., 3rd ed., 1964, pp. 37–39, 287–289.
Williams, Methods in Immuno & Immunochem., Academic Press, N.Y., vol. III, 1971, pp. 370–374.

*Primary Examiner*—Albert T. Meyers
*Assistant Examiner*—A. P. Fagelson
*Attorney, Agent, or Firm*—Knobbe, Martens, Olson, Hubbard & Bear

[57] ABSTRACT

Erythrocytes derived from certain animal or fowl blood are specially treated to produce a substance which is readily agglutinable by viruses and by certain types of antibodies. The substance possesses properties of stability, sensitivity and agglutinability which are utilized in a serological diagnostic test for viral diseases.

3 Claims, No Drawings

METHOD FOR THE DIAGNOSIS OF VIRAL DISEASES

This is a division, of application Ser. No. 112,039, filed Feb. 2, 1971, now U.S. Pat. No. 3,777,014, which is a continuation-in-part of application Ser. No. 786,770, filed Dec. 24, 1968, now abondoned.

DESCRIPTION OF THE INVENTION

This invention relates to the provision of a serological diagnostic test for viral diseases, and more particularly, to a process for preparing reagents for use in the test and the method of performing the test. The test is useful in the diagnosis of viral infections, including mumps, influenza, rubella, those forms of encephalomyelitis known as WEE, EEE and VEE, St. Louis and J.B. encephalitis, poliomyelitis, herpes and others.

Three main serological tests have been used for the diagnosis of viral diseases. They are the complement fixation, the hemagglutination-inhibition (called HI) and the virus neutralization tests. These tests however have many shortcomings. They are difficult to perform, requiring highly trained personnel. Most of the reagents are costly, unstable and difficult to prepare. The tests require costly equipment and are time-consuming (i.e. they involve several hours of elapsed time before the test results are available). For these reasons they can be performed only by laboratories that are highly specialized and equipped in virology.

It is a primary object of this invention to provide a diagnostic test for viral diseases which utilizes reagents which are more sensitive and specific to virus reactions than those used heretofore, and which accordingly function quickly to detect the presence of specific antibodies in the patient's blood. An allied object is to provide such a test which can be carried out so quickly that the test results are available in a few minutes time.

Another object of the invention is to provide a diagnostic test which may be routinely employed, e.g. in large and small hospitals, clinics, and public health laboratories, without need of elaborate and costly laboratory facilities.

Still another object is to provide a diagnostic test which gives accurate and reliable results and can be used to detect any of a number of different viral diseases.

It is yet another object of the invention to provide a diagnostic test which utilizes reagents having a very long shelf life, viz. up to 1 year or longer.

Other objects and advantages of the invention will become apparent upon reading the attached detailed description.

In carrying out the invention certain raw animal or fowl blood cells are specially treated to produce a substance which possesses properties which enable it to be readily agglutinated by such viruses (as well as by certain antibodies). This substance is then utilized to detect the presence of specific antibodies in the serum of a patient. In accordance with the custom in immunology, serology and other scientific fields, I call this new antigen the Zichis Antigen.

In the procedure a specific viral antigen is prepared and standardized. The patient's serum, suspected to contain antibodies, is mixed with the viral antigen. Then the aforementioned special agglutinable substance, which I call Zichis Antigen, is added to the mixture.

The presence or absence of a visible agglutination reaction in the mixture within just a few minutes time signifies the test results. The presence of agglutination indicates a negative diagnosis. Absence of agglutination indicates a positive diagnosis.

In a positive test the patient's serum contains specific antibodies which neutralize the virus so that agglutination does not occur when the agglutinable substance is added. In a negative test specific antibodies are absent from the patient's serum and the viral antigen is not neutralized. When the Zichis Antigen is added it becomes agglutinated by the viral antigen.

In many viral diseases it is possible to grow the virus in tissue culture, embryonated egg, or animals in a short period of time. It has been found that the Zichis Antigen is agglutinated by such virus growths. Then by using specific viral antisera the virus may be identified by this procedure. Thus the diagnosis may be made in a relatively short time. Such a test may be used, for example, in influenza and mumps.

The preparation and standardization of the various reagents used in the test may be carried out as described below.

The Zichis Antigen

The Zichis Antigens are prepared from either animal or fowl erythrocytes. Erythrocytes derived from various animals or fowl may be used. For example rat, mouse, pig, dog or guinea pig erythrocytes may be used, as may chicken, one day old chick, goose (especially male), pigeon, swan or duck erythrocytes.

The Zichis Antigens usually have broad agglutinable properties, but they react selectively with viruses depending on the source of the erythrocytes used to prepare the antigen. For example, a Zichis Antigen prepared from guinea pig erythrocytes will be agglutinated by the influenza, mumps and poliomyelitis viruses but not by the rubella virus. On the other hand, if the Zichis Antigen is prepared from one day old chick erythrocytes it is agglutinated by the rubella virus. In the case of any given virus it therefore will be necessary to establish which particular Zichis Antigen (i.e. from which specific erythrocyte source) will be agglutinated by that virus. This may readily be done by trial and error using the slide method which is described below.

The Zichis Antigen is prepared by treating selected animal or fowl erythrocytes with an aqueous solution containing borate ions preferably along with a suitable anti-contaminant which prevents the growth of microorganisms that may affect the antigen and in this sense acts as a preservative, such as sodium azide, and a suitable agent for enhancing the isotonic character of the solution (e.g. sodium chloride). The solution should be isotonic and neutral, i.e. have a PH close to 7. After treatment the mixture is incubated and the sediment, containing the Zichis Antigen, is separated out.

Various combinations of acids and salts capable of producing borate ions in solution may be used. Thus combinations of a borate salt of an alkali metal, e.g. sodium borate, with an acid such as ascorbic or isoascorbic, acetic or hydrochloric acid have been used successfully. One particularly useful combination is boric acid and sodium hydroxide.

Although the exact mechanism is not understood, I find that the technique which I employ, involving treatment with borate ions in a neutral and isotonic solution, results in the Zichis Antigen.

One representative way in which the Zichis Antigen may be prepared is as follows:

1. The animal or fowl erythrocytes are added to a water solution containing 3,8% by weight of sodium citrate. Preferably a 5 to 6 volume ratio is used of blood to sodium citrate solution, since this ratio has been found to prevent coagulation. The resulting suspension is then washed thoroughly with cold (e.g. about 3° C.) physiological saline solution to remove the sodium citrate, the plasma and soluble salts of the blood. For example it has been found that one washing, using a 10 to 1 volume ratio of physiological saline solution to blood, is satisfactory. If desired other anti-coagulants than sodium citrate may be used.

2. A water solution is prepared containing 2000 cc. of distilled water, 60 gms. of boric acid (USP Grade), 80 cc. of 1.0 N sodium hydroxide (CP Grade), 4 gms. of sodium azide (Tech. Grade), and 18 gms. of sodium chloride (CP Grade). The pH should be adjusted to approximately seven if necessary, using either boric acid or sodium hydroxide solution whichever; is required.

3. The solution prepared in step 2. is cooled to about 2° to 4° C. If the temperature is above about 4° C., there will be undesirable loss in sensitivity of the final Antigen.

4. The erythrocytes from 100 cc. of the animal or fowl blood (step 1.) are then added to the cooled solution of step 3. If the pH of the resulting mixture changes from about seven, it should be adjusted to seven in this case by adding more boric acid or sodium hydroxide.

5. The resulting mixture is incubated at about 2° to 4° C., with stirring either continuously or at intervals (e.g. three times a day) to prevent settling of the cells. If continuous agitation is employed the incubation time will tend to be reduced. Continue incubation until the formation of a white-grayish layer (the antigen) is observed. This usually occurs within 8 to 20 days. Allow the antigen formation to continue for about 3 additional days.

6. After incubation as described in step 5., stir the mixture and centrifuge for 30 minutes at 4500 r.p.m. to separate the antigen from the remaining materials such as the hemoglobin, plasma, cell proteins and sodium citrate. Centrifugation produces three layers, a bottom layer of heavy cellular material, middle layer of the white-grayish material which contains the antigen, and a top layer of supernatant liquid.

7. Discard both the supernatant liquid (top layer) and the heavy cellular material (bottom layer). Wash the middle layer, containing the antigen, with saline solution by centrifugation, once more discarding top and bottom layers and retaining the middle antigen containing layer. Repeat the washing until the supernatant is clear (indicating that the hemoglobin and other separated materials (see step 6. above) have been removed.) Usually three washings suffice.

8. The white-grayish sediment constitutes the special Zichis Antigen. The antigen is taken up in 20 cc. of saline solution, and preserved by adding 0.2% by weight sodium azide.

Viral Antigen

The specific viral antigen may be obtained from any of several sources, viz. tissue culture, infected animal tissue or infected tissue of developing hen's eggs. It may be prepared from the crude form using well known physical or chemical methods. The virus in the antigen should be in a relatively pure and concentrated form (e.g. in mumps start with an agglutination titer of about 1-20 and concentrate to about 1-5000). For safety reasons the virus is inactivated (to destroy its infectivity while preserving its antigenicity) using known techniques, e.g. by ultra-violet light or chemical methods (e.g. formalin, phenol, cresol, beta propiolactone).

Standardization of the Viral Antigen Against the Zichis Antigen

This is a quantitative test, and for this reason the smallest quantity of virus antigen that is required for agglutination must be established. Accordingly it is necessary to find the highest dilution of viral antigen which still produces an easily observable agglutination reaction with the Zichis Antigen. This is done by standardizing the viral antigen against the Zichis Antigen by dilution. Standardization may be carried out as follows:

1. Make serial dilutions of the viral antigen in physiological saline solution from one part viral antigen to two parts saline solution to one part viral antigen to 512 parts saline solution. It may be necessary to use even higher dilutions of the viral antigen in some cases.

2. Place a drop of each dilution on a separate square marked on a glass plate.

3. To each such drop, add a drop of the Zichis Antigen.

4. Mix the reagents on each square with separate wooden applicators (or use a single applicator, going from high to low dilution).

5. Rotatively manipulate the glass plate over an indirect light and observe the agglutination reactions.

6. The last dilution which shows distinct agglutination (i.e. when the next higher dilution produces no agglutination) represents what I define as one agglutinative unit of viral antigen.

For the diagnostic test I recommend using the smallest amount of viral antigen (gives highest sensitivity of test) that still permits easy reading of the agglutination reaction. I have found that the second last dilution, i.e. the dilution that represents two agglutinative units of viral antigen, is usually satisfactory. In some instances it may be that four agglutinative units of viral antigen should be used to facilitate reading of the reaction.

Pre-Treatment of Patient's Serum

Usually normal sera contain substances which non-specifically prevent agglutination such as experienced in the hemagglutination-inhibition test with raw crythrocytes. The patient's serum must accordingly be treated, using known techniques, to remove these non-specific agglutination inhibitors. This may be done using one of the following known techniques: kaolin, $CO_2$, heparin, receptor destroying enzyme or rivanol.

Test

The diagnostic test which results from practice of this invention is carried out using the below described test procedure.

A drop of the patient's pre-treated serum is placed on a glass plate.

A drop of the separately prepared and standardized viral antigen is added to the drop previously placed on the glass plate.

The two reagents (drops) are mixed with a wooden applicator and allowed to stand for about 2 minutes.

Then a drop of the Zichis Antigen is added to the mixture, and mixing is carried out as before.

Finally the glass plate is rotatively manipulated gently over an indirect light for not more than about 2 minutes, and the presence or absence of agglutination reactions is visually observed.

In a positive test, the viral antigen will have been neutralized by the specific antibodies in the patient's serum, and no agglutination occurs with the Zichis Antigen.

In a negative test, agglutination will be observed since the patient's serum does not contain the specific antibodies and the viral antigen remains free to agglutinate the Zichis Antigen. The agglutination if present ranges from coarse to light, and is easily visible to the naked eye.

If the test is positive it is of course necessary to establish the antibody titer of the serum to make sure that the test results are meaningful. This may be done by making up serial dilutions of the serum in physiological saline solution and then determining the lowest dilution (titer) at which an agglutination reaction is observed (viz. at this point there are not enough serum antibodies present to neutralize the virus, so that agglutination occurs).

If the test results are positive, a later (e.g. 6 1 to 10 days later) specimen of serum should be tested for titer to provide a definite diagnosis. A confirming diagnosis results if the later specimen has an antibody titer higher than that of the first specimen, indicating that an active infection in the patient is developing additional antibodies with time.

Inasmuch as my test herein described involves specific agglutination as well as inhibition of such agglutination resulting from reaction with a specific antiserum, and is carried out utilizing the slide technique, I propose to name my test the Viral Slide Agglutination-Inhibition Test (VSAI).

Over seven hundred sera in cases involving mumps studies have been tested according to the present invention on a comparative basis with conventional techniques, namely with the HI (hemagglutination-inhibition), CF (complement fixation) and neutralization tests. Similarly several hundred such comparative tests have been made on sera from influenza cases. It was found that both positive and negative test results using the conventional techniques were confirmed in every instance by use of my Viral Slide Agglutination-Inhibition Test. In addition it was found that my test in a number of instances was found to be two or four times more sensitive than the HI test.

It will be seen that my invention depends on my observation that neutralization of the viral antigen by the specific serum takes place on a slide without visible agglutination, thus rendering meaningful the agglutination resulting from the addition of the Zichis Antigen in the test procedure and making it possible to use the simple, quick slide test technique described herein.

The hereindescribed diagnostic test has wide applicability to detection of many different viral diseases. In addition to being responsive to the presence of viral antibodies or viruses, the Zichis Antigen described herein is agglutinable by certain other antibodies. For example this substance is agglutinable by antibodies associated with syphylis and may be used for the diagnosis of that disease.

Quite apart from the instant diagnostic test, the procedure set forth herein for preparation of the Zichis Antigen may also be used to advantage in virus purification techniques in which a virus is absorbed on the Zichis Antigen and then eluted in a clean and concentrated form.

While the invention has been described in conjunction with specific embodiments thereof, it is evident that many alternatives, modifications, and variations will become apparent to those skilled in art in light of the foregoing description. Accordingly, it will be understood that the definition of the invention is set forth in the attached claims and that I do not intend to limit the invention to the particular embodiments described.

I claim as my invention:

1. A seriological diagnostic slide test for viral diseases comprising the steps of:
   obtaining an aliquot of human blood serum which is suspected to contain particular viral antibodies;
   placing on a slide said aliquot of human blood serum in the presence of a viral antigen which is specific to the virus which produces said antibodies so that neutralization takes place on the slide between the viral antigen and the specific serum without visible agglutination;
   then adding on the slide to said mixture an antigen prepared from erythrocytes characterized by being readily agglutinated by a virus, being free of hemoglobin, and being agglutinative with the viral antigen; and
   observing the results, in the case of a positive test, the absence of agglutination, and in the case of a negative test, the presence of agglutination.

2. A serological diagnostic test for viral diseases comprising the steps of:
   obtaining an aliquot of human blood serum which is suspected to contain particular viral antibodies;
   placing said aliquot of human blood serum in the presence of a viral antigen which is specific to the virus which produces said antibodies so that neutralization takes place between the viral antigen and the specific serum without visible agglutination;
   then adding to said mixture an antigen which is free of hemoglobin and agglutinative with the viral antigen, said antigen prepared by separating erythrocytes from animal or fowl blood to remove plasma and anticoagulant, treating the erythrocytes with an isotonic aqueous solution having a pH of about 7 and containing borate ions and boric acid and a preservative, incubating the resulting mixture of erythrocytes and isotonic solution at about 2° to about 4° C for about 8 to 23 days, and separating the resulting stable serologically active white-grayish antigen from the residual liquid and blood substances; and
   observing the results, in the case of a positive test, the absence of agglutination, and in the case of a negative test, the presence of agglutination.

3. A serological diagnostic test for viral diseases as defined in claim 2 wherein the neutralization between the human blood serum and the viral antigen and the agglutination with the viral antigen is carried out on a slide.

* * * * *